United States Patent [19]

Simon et al.

[11] Patent Number: 4,568,468
[45] Date of Patent: Feb. 4, 1986

[54] USE OF NORBORNANE DERIVED COMPOUNDS AS THRESHOLD AGENTS

[75] Inventors: Jaime Simon, Angleton; Druce K. Crump, Lake Jackson; David A. Wilson, Richwood, all of Tex.

[73] Assignee: The Dow Chemical Company, Midland, Mich.

[21] Appl. No.: 695,604

[22] Filed: Jan. 28, 1985

Related U.S. Application Data

[62] Division of Ser. No. 584,071, Feb. 27, 1984, Pat. No. 4,500,469.

[51] Int. Cl.$^4$ ............................................. C02F 5/14
[52] U.S. Cl. ................................... 210/700; 252/180
[58] Field of Search ............... 210/699, 700, 698; 252/180, 181; 260/502.5 E, 501.11, 501.12, 503; 562/502; 564/456

[56] References Cited

U.S. PATENT DOCUMENTS

| | | | |
|---|---|---|---|
| 2,599,807 | 6/1952 | Bersworth | 260/500 |
| 2,609,390 | 9/1952 | Bersworth | 260/500 |
| 3,288,846 | 11/1966 | Irani et al. | 260/500 |
| 3,331,773 | 7/1967 | Gunderson et al. | |
| 3,336,221 | 8/1967 | Ralston | |
| 3,434,969 | 3/1969 | Ralston | |
| 3,674,804 | 7/1972 | Redmore | 260/309.6 |
| 3,720,498 | 3/1973 | Redmore | 422/15 |
| 3,743,603 | 7/1973 | Redmore | 252/180 |
| 3,859,211 | 1/1975 | Redmore | |
| 3,954,761 | 5/1976 | Redmore | 260/268 K |
| 4,035,412 | 7/1977 | Quinlan | 260/502.5 E |
| 4,051,110 | 9/1977 | Quinlan | 260/72 R |
| 4,500,469 | 2/1985 | Simon et al. | 210/700 |
| 4,500,470 | 2/1985 | Wilson | 210/700 |

FOREIGN PATENT DOCUMENTS 750481  6/1956  United Kingdom ......... 260/502.5 E

OTHER PUBLICATIONS

Proc. Int. Water. Conf., Eng. Soc. West Pa., 41, pp. 167–174, 1980, "Toward a Better Understanding of Commercial Organophosphonates", Campbell.

Proc. Int. Water. Conf., Eng. Soc., West Pa., 39, pp. 89–99, 1978, "Scale & Deposit Control in Cooling Water Systems," Townsend et al.

Hoechst Organic Chemicals Brochure Title Page and pp. 4, 14, & 15.

*Primary Examiner*—Peter Hruskoci
*Attorney, Agent, or Firm*—A. C. Ancona

[57]  ABSTRACT

A process of preventing precipitation of scale producing metal ions, e.g. calcium, from their aqueous solutions by adding an effective amount of a methylenephosphonic acid derivative of bis(methylamine)-norbornane. These compounds are effective in threshold amounts.

6 Claims, No Drawings

USE OF NORBORNANE DERIVED COMPOUNDS AS THRESHOLD AGENTS

This is a divisional of application Ser. No. 584,071, filed Feb. 27, 1984, now U.S. Pat No. 4,500,469.

BACKGROUND OF THE INVENTION

Norbornane is a cyclic compound found in or derivable from the residual heavy hydrocarbons in the bottoms of distillation towers in light hydrocarbon production facilities. Various derivatives of norbornane have been made, among them the bis(methylamine). It is this compound which has been phosphonomethylated which is the subject of the present invention.

It is well known that amines such as ethylenediamine and diethylenetriamine can be reacted with formaldehyde and phosphorus acid to obtain methylene phosphonate derivatives of the amine in which the methylene phosphonate group

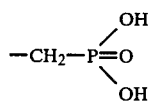

substitutes for the amine hydrogens (U.S. Pat. No. 3,288,846).

The use of methylenephosphonic acid substituted alkylene polyamines for metal ion control at less than stoichiometric amounts was suggested in a patent (U.S. Pat. No. 2,609,390) issued in 1952. Later a water dispersible polymeric amine chelating agent which included alkylene phosphonate derivatives was indicated as having "threshold" effects in scale inhibition applications (see U.S. Pat. No. 3,331,773), this term being used to describe the use of the agent in less than stoichiometric amounts. The diamine and polyamine methylenephosphonate derivatives are taught and claimed in U.S. Pat. Nos. 3,336,221 and 3,434,969, respectively. Some of the products disclosed in these two patents are available commercially and are recommended as scale inhibitors when applied in threshold amounts.

Other patents which disclose heterocyclic nitrogen containing compounds which are useful as chelating agents and may be employed in threshold amounts are U.S. Pat. Nos. 3,674,804; 3,720,498; 3,743,603; 3,859,211; and 3,954,761. Some of the compounds included therein are heterocyclic compounds having the formulas:

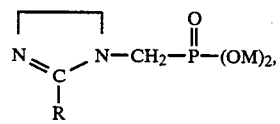

wherein R is hydrogen or alkyl and M is hydrogen, alkali metal, ammonium or a di- or triethanolamine radical;

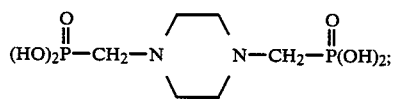

-continued

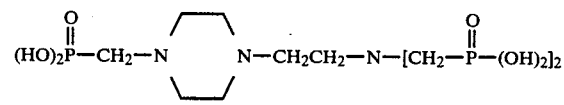

and

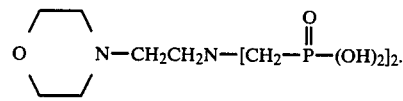

Certain phosphonic acid derivatives of the aliphatic acids can be prepared by reacting phosphorous acid with acid anhydrides or acid chlorides, e.g. the anhydrides or chlorides of acetic, propionic and valeric acids. The compounds prepared have the formula

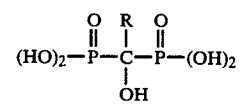

wherein R is a lower alkyl radical having 1 to 5 carbon atoms. The method of making and use of these products is described in U.S. Pat. No. 3,214,454. The use of threshold amounts to prevent calcium precipitation is disclosed and claimed therein.

It has now been discovered that new chelating and threshold agents for inhibiting precipitation of metal ions can be made from the bis(methylamine) derivatives of norbornane. This compound has the structure

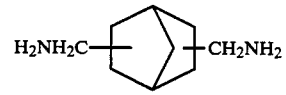

This compound is also known by the more formal name of 2(3), 5(6)-bis[aminomethyl]bicyclo(2,2,1)heptane. Its derivatives are those with various substituents replacing the primary amine hydrogens.

SUMMARY OF THE INVENTION

A new class of compounds is formed when norbornane bis(methylamine) is reacted with certain compounds, e.g. formaldehyde and phosphorous acid will form methylenephosphonic acid derivatives. These new compounds have the structure

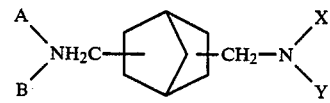

wherein substituents A, B, X and Y each are independently selected from radicals consisting of hydrogen, hydroxyalkyl (wherein the alkyl group contains 2–6 carbon atoms), methylenephosphonic, methylene-, ethylene- and propylenesulfonic 2-hydroxypropylsulfonic and carboxylic acid radicals (having 2–4 carbon atoms) and the alkali or alkaline earth metal, ammonia and amine salts of any of the phosphonic, sulfonic or carboxylic acid derivatives. At least one of the substituents must be other than a hydrogen.

DETAILED DESCRIPTION OF THE INVENTION

The following examples illustrate the preparation and use of the new compounds of the invention. Identification of the compounds is made by reference to the above structure.

EXAMPLE 1

Distilled water (10 g) and $H_3PO_3$ (9.9 g) were weighed into a 50-ml round-bottom flask equipped with a water-cooled condenser, a thermometer, a stirring bar, and an addition funnel. Concentrated HCl (11.8 g) was then added and 3.9 g of 2(3),5(6)bis[aminomethyl]-bicyclo(2,2,1)heptane was slowly added while stirring. The solution was heated at reflux for approximately one hour and a 37% aqueous formaldehyde solution (8.51 g) was added over a period of 2.5 hours. The solution was heated for an additional 3 hours at reflux. The compound formed was the completely phosphonomethylated norbornane derivative wherein each of A, B, X and Y were methylenephosphonic acid groups, —$CH_2PO_3H_2$.

EXAMPLE 2

The procedure for Example 1 was followed for the addition of 3 mole equivalents of $CH_2O$ (24.3 g of a 37% solution) and phosphorous acid (25.1 g) to one mole equivalent of 2(3),5(6)bis[aminomethyl]bicyclo(2,2,1-)heptane (15.2 g). The resultant solution was neutralized with NaOH (aq) and one mole equivalent of glycolonitrile (14.7 g of a 38% solution) and NaOH (13.8 g of a 33.3% solution) was added. The compound formed was the sodium salt of the bicycloheptane derivative which had an average of three methylenephosphonic acid groups and one carboxymethyl group per molecule as the A, B, X and Y substituents.

EXAMPLE 3

A quantity (15.2 g, 0.1 mole) of 1(2),4(5)bis[aminomethyl]bicyclo(2,2,1)heptane was placed into a stainless steel beaker and 50 ml of distilled water was added, followed by the addition 37 ml of 50% NaOH. This solution was heated to $\sim 70°$ C. with stirring and carboxymethylation accomplished by adding dropwise 58.9 g of 38% glycolonitrile while still heating, over a one-hour period. After $\sim 15$ minutes of the addition, the temperature was at reflux and $NH_3$ was being liberated. Distilled water was added periodically to replace the evaporated water. After completing the addition of glycolonitrile, the solution was heated for an additional hour while stirring and purging with $N_2$. The compound formed was the tetracarboxymethyl derivative wherein A, B, X and Y are $CH_2$—COONa.

The utility of the compounds of the invention was ascertained by conducting scale inhibition tests according to National Association of Corrosion Engineers (NACE) test method TM-03-74. The calcium carbonate scale inhibition results are shown in Table I and compared with a commercially available scale inhibitor, aminotri(methylenephosphonic acid). Calcium sulfate scale inhibition was also tested and results are shown in Table II.

TABLE I

Calcium Carbonate Scale Inhibition Data

| Compound | Concentration* | % of $Ca^{++}$ Remaining in Solution at | | |
|---|---|---|---|---|
| | | 24 Hrs | 48 Hrs | 72 Hrs |
| None | — | 54 | 53 | 52 |
| Example 1 | 10 ppm | 96 | 94 | 86 |
| Example 2 | 10 ppm | 94 | 82 | 79 |
| aminotri(methylene-phosphonic acid) | 10 ppm | 94 | 82 | 79 |

TABLE II

Calcium Sulfate Scale Inhibition Data

| Compound | Concentration* | % of $Ca^{++}$ Remaining in Solution at | | |
|---|---|---|---|---|
| | | 24 Hrs | 48 Hrs | 72 Hrs |
| None | — | 67 | 65 | 65 |
| Example 1 | 1 ppm | 100 | 99 | 99 |
| Example 2 | 1 ppm | 99 | 99 | 98 |
| aminotri(methylene-phosphonic acid) | 1 ppm | 84 | 80 | 77 |

The usefulness of the compounds of the present invention to act as chelating agents was demonstrated by titrating the compounds with standard copper solution in the presence of chrome azurol-S indicator. The compound of Example 1 was titrated and found to complex approximately 1.5 moles of copper per mole of ligand. This compound can function as either a threshold compound or a chelating agent.

It should be recognized that the compounds of the invention can have several different groups as the A, B, X and Y substituents on the same molecule, but that when mixed derivatives are obtained, it is not usually possible to direct or predict which amine hydrogens are substituted. The product, in all probability, contains a mixture of isomeric compounds.

While all of the compounds will chelate metal ions, only those which contain at least one methylenephosphonic acid group or its salt will provide a threshold effect.

I claim:

1. A process for inhibiting the precipitation of scale producing metal ions from their aqueous solutions which comprises adding to said solutions in less than stoichiometric amounts, based on the metal ions present, an effective amount of compound of the formula

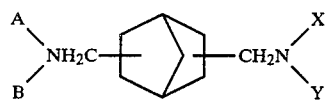

wherein substituents A, B, X and Y each are independently selected from radicals consisting of hydrogen, hydroxyalkyl (wherein the alkyl group contains 2-6 carbon atoms), methylenephosphonic; methylene-, ethylene- and propylenesulfonic; 2-hydroxypropylsulfonic; alkylcarboxylic acid radicals (having 2-4 carbon atoms) and the alkali, alkaline earth metal, ammonium and amine salts thereof and wherein at least one of said substituents is a methylenephosphonic acid radical or a salt thereof.

2. The process of claim 1 wherein the substituent salt of the methylenephosphonic acid radical is an alkali metal salt.

3. The process of claim 1 wherein the substituent salt of the methylenephosphonic acid is an amine salt.

4. The process of claim 1 wherein the substituent salt of the methylenephosphonic acid is an alkaline earth metal salt.

5. The process of claim 4 wherein the alkaline earth metal is magnesium, calcium or barium.

6. The process of claim 1 wherein the substituent salt of the methylenephosphonic acid is an ammonium salt.

* * * * *

UNITED STATES PATENT AND TRADEMARK OFFICE
CERTIFICATE OF CORRECTION

PATENT NO. : 4,568,468

DATED : February 4, 1986

INVENTOR(S) : Jaime Simon, Druce K. Crump and David A. Wilson

It is certified that error appears in the above-identified patent and that said Letters Patent is hereby corrected as shown below:

Col. 3, line 53; change "are" to --were--.

Col. 4, line 19; add the following footnote immediately after Table II:   --*ppm based on active acid--.

Col. 4, line 41, Claim 1; insert --a-- between "of" and "compound".

Signed and Sealed this

Eleventh Day of November, 1986

Attest:

DONALD J. QUIGG

Attesting Officer          Commissioner of Patents and Trademarks